United States Patent [19]

Shimomura et al.

[11] Patent Number: 5,263,982
[45] Date of Patent: Nov. 23, 1993

[54] HOLLOW FIBER MEMBRANE TYPE ARTIFICIAL LUNG

[75] Inventors: Yasushi Shimomura, Chiba; Masahiko Yamaguchi; Akio Funakubo, both of Ichihara, all of Japan

[73] Assignee: Ube Industries, Ltd., Ube, Japan

[21] Appl. No.: 668,562

[22] Filed: Mar. 13, 1991

[30] Foreign Application Priority Data

| Mar. 14, 1990 [JP] | Japan | 2-63408 |
| Jul. 17, 1990 [JP] | Japan | 2-187101 |
| Aug. 10, 1990 [JP] | Japan | 2-210291 |
| Aug. 31, 1990 [JP] | Japan | 2-228389 |
| Sep. 19, 1990 [JP] | Japan | 2-249682 |

[51] Int. Cl.$^5$ .............. A61F 2/04; A61M 37/00
[52] U.S. Cl. .............. 623/12; 604/4
[58] Field of Search .............. 604/4, 5; 623/12

[56] References Cited

U.S. PATENT DOCUMENTS

| 3,489,647 | 1/1970 | Kolobow | 604/5 X |
| 3,887,427 | 6/1975 | Helmer et al. | 162/158 |
| 3,901,808 | 8/1975 | Bokros | 604/4 X |
| 3,931,069 | 1/1976 | Lundin | 162/158 X |
| 3,990,939 | 11/1976 | Aldrich et al. | 162/158 X |
| 4,207,142 | 6/1980 | Shepherd | 162/158 |
| 4,214,948 | 7/1980 | Mazzarella et al. | 162/158 |
| 4,240,935 | 12/1980 | Dumas | 162/158 X |
| 4,243,481 | 1/1981 | Dumas | 162/158 |
| 4,248,736 | 2/1981 | Fuchigani et al. | 604/4 X |
| 4,295,931 | 10/1981 | Dumas | 162/158 |
| 4,317,756 | 3/1982 | Dumas | 162/158 X |
| 4,517,090 | 5/1985 | Kersten et al. | 604/4 X |
| 4,559,034 | 12/1985 | Kirita et al. | 604/5 X |
| 4,568,327 | 2/1986 | Seufert | 604/5 |
| 4,631,053 | 12/1986 | Taheri | 604/4 X |
| 4,642,089 | 2/1987 | Zupkas et al. | 604/4 |
| 4,650,457 | 3/1987 | Morioka et al. | 604/4 |
| 4,676,771 | 6/1987 | Henke | 604/4 |
| 4,732,675 | 3/1988 | Badolato et al. | 604/5 X |
| 4,770,852 | 9/1988 | Takahara et al. | 623/12 X |
| 4,861,485 | 8/1989 | Fecondini | 604/5 X |
| 4,964,915 | 10/1990 | Blixt et al. | 106/210 |
| 4,986,809 | 1/1991 | Hatter | 604/4 X |

FOREIGN PATENT DOCUMENTS

| 0103899 | 3/1984 | European Pat. Off. | 623/12 |
| 0167162 | 1/1986 | European Pat. Off. | |
| 0209465 | 1/1987 | European Pat. Off. | 623/12 |
| 0299381 | 1/1989 | European Pat. Off. | 623/12 |
| 0097172 | 4/1988 | Japan | 623/12 |
| 0006538 | 2/1990 | Japan | 623/12 |

OTHER PUBLICATIONS

'Artificial "Membrane Lung"'; Biomed. Eng (USA), vol. 10, No. 4 (Jul.-Aug. 1976), (Publ. Mar. 1977), pp. 236-240.
Japanese Patent Abstract, vol. 13, No. 179, (C-590) [3527] Apr. 26, 1989, of JP-A-7907, Jan. 1, 1989 (Daicel Chem. Ind. Ltd.).
Hercules, Inc. on Benefits of Using Aquapel.
D. Sizing with Alkylketene Dimers, W. O. Kincannon Jr and S. H. Watkins, Special Sizes.

Primary Examiner—David Isabella
Assistant Examiner—Elizabeth M. Burke
Attorney, Agent, or Firm—Armstrong, Westerman, Hattori, McLeland & Naughton

[57] ABSTRACT

The hollow fiber membrane type ariticial lung has an inner cylinder, an outer cylinder, a hollow fiber bundle formed by collecting porous hollow fiber membrane and a supporting member for liquid-hermetically supporting the outer surface of the inner cylinder, the inner surface of the outer cylinder and the outer surface of the hollow fiber membrane at the two ends of the inner cylinder, the outer cylinder and the hollow fiber bundle in such a manner that the hollow fiber membrane is opened. The arificial lung reveals a reduced pressure loss and is capable of preventing blood channeling, and exhibit an excellent gas exchanging efficiency.

3 Claims, 9 Drawing Sheets

HOLLOW FIBER MEMBRANE TYPE ARTIFICIAL LUNG

BACKGROUND OF THE INVENTION

1. Field of the Invention:

The present invention relates to a hollow fiber membrane type artificial lung of an externally blood-flowing type in which blood flows outside, a hollow fiber membrane and oxygen is introduced into a space of the hollow fibers membrane and a fiber arrangement method therefor. More particularly, the present invention relates to a hollow fiber membrane type artificial lung revealing a reduced pressure loss, capable of preventing blood channeling (a phenomenon of a nonuniform blood flow while being deviated locally), exhibiting an excellent gas exchanging efficiency and significantly reduced size and displaying an advantage in that a necessary quantity of blood to be enclosed can be reduced.

2. Description of the Related Art:

An artificial lung has been used to perform blood gas exchange at the time of a heart opening operation. Artificial lungs are exemplified by a bubble type artificial lung and a membrane type artificial lung. The bubble type artificial lung is arranged to introduce a gas into blood, and blood and the gas are thereby directly brought into contact with each other. In consequence, a problem arises in that blood corpuscles will be broken, that is, hemolysis takes place. On the other hand, the membrane type artificial lung is arranged to perform the blood gas exchange via a gas permeable membrane. Therefore, it is widely clinically used since the membrane type artificial lung is a rather physiological method in comparison to the bubble type artificial lung.

The membrane type artificial lung uses a gas permeable hollow fiber membrane for most part, the membrane type artificial lung being exemplified by an internal flow system in which blood flows in a space in the hollow fiber membrane and an external flow system in which the same flows outside the hollow fiber membrane. The internal flow system is arranged in such a manner that blood flows in a space in the hollow fiber membrane the fiber having an extremely small diameter of several tens to several hundred of $\mu s$. Therefore, an excessively large pressure loss takes place when blood circulates, causing the blood corpuscles to be damaged. Namely, the hemolysis will take place. What is even worse, blood flowing in the portions except for the portion near the surface of the membrane cannot easily be oxidized since blood flows in the form of a laminar flow. Therefore, an excessively large membrane area must be given in order to improve the gas exchanging performance. In consequence, the quantity of blood to be charged, that is, the quantity of blood to be circulated outside the body is enlarged excessively.

When a centrifugal pump or a pulsation flow pump which has been used recently is used to perform the body outside circulation, the pressure loss in the artificial lung must be reduced as much as possible. Therefore, it is preferable to employ the external flow system.

In the external flow system, blood flows outside the hollow fiber membrane. As a result, the problems experienced with the above-described internal flow system can be overcome. However, another problem arises in that the blood flow will deviate to a passage having relatively small resistance (a so-called channeling takes place). In consequence, the gas exchanging performance of the artificial lung will excessively deteriorate. Accordingly, a structure in which the hollow fibers are twilled or another structure in which the hollow fibers are woven have been developed in order to prevent the drift of the blood flow. In addition, although a structure in which the hollow fibers are arranged linearly has been developed, an excessively precise task must be performed to uniformly arrange the hollow fibers. In the structure in which the hollow fibers are twilled or the structure in which the same are woven, the blood flow becomes too complicated. In consequence, an excessively large resistance is generated when blood flows, and the pressure loss becomes excessively large. In the structure in which the hollow fibers are arranged linearly, the same cannot satisfactorily equally be arranged. Therefore, the membrane area must be enlarged in order to improve the gas exchanging performance. If the membrane area is enlarged for the purpose of overcoming the abovedescribed problem, the necessary quantity of blood to be filled in the artificial lung is enlarged. In consequence, a problem arises in that the body outside circulation operation cannot be easily performed without a blood transfusion.

The above-described problems are considerably influenced by a state where the hollow fibers is arranged in a bundle, the packing ratio, the positions of the blood inlet and outlet ports and the blood passage. Accordingly, there have been a method for improving the gas exchanging efficiency and the pressure loss by enlarging the area of the membrane or enlarging the area of the fluid passage and another method capable of reducing the pressure loss by allowing blood to flow in the side portion of the hollow fiber bundle. However, the former method encounters a problem in that a large quantity of blood must be enclosed although the pressure loss can be prevented. Another problem arises in the latter method in that it cannot easily be combined with a pulsation pump or the like although the pressure loss can be further prevented in comparison to the pressure loss taken place in the internal flow system.

Another structure has been disclosed which is arranged in such a manner that the hollow fiber membrane is wound around a cylindrical member to form a bundle so as to prevent the blood drift and to obtain an excellent gas exchanging performance. However, that structure generates an excessively large pressure loss since blood, which has been supplied from the blood port through a blood inlet (a portion through which blood is introduced into the hollow fiber bundle), is rapidly introduced into the hollow fiber bundle and, what is even worse, the flow passage is rapidly narrowed. If the blood inlet is enlarged in order to prevent that problem, the overall size of the artificial lung is excessively enlarged.

SUMMARY OF THE INVENTION

Accordingly, an object of the present invention is to provide a hollow fiber membrane type artificial lung capable of the above-described conventional problems.

According to one aspect of the present invention, there is provided a hollow fiber membrane type artificial lung having a casing which accommodates a hollow fiber bundle and a potting material for supporting and securing the hollow fiber bundle at positions near the two ends of the casing in such a manner that the two ends of hollow fiber membrane bundle are opened, wherein a gas containing oxygen flows in a space in the hollow fiber membrane and blood flows in a space formed by the outer wall of the hollow fiber membrane and the inner wall of the casing, the hollow fiber membrane type artificial lung comprising: a substantially overall internal space of the casing in which the hollow fiber membrane bundle is packed.

According to another aspect of the present invention, there is provided a hollow fiber membrane type artificial lung having an inner cylinder, an outer cylinder, a hollow fiber bundle formed by collecting porous hollow fibers membrane and a supporting member for fluid-hermetically supporting the outer surface of the inner cylinder, the inner surface of the outer cylinder and the outer surface of the hollow fiber bundle at the two ends of the inner cylinder, the outer cylinder and the hollow fiber bundle in such a manner that the hollow fiber membrane is opened, the hollow fiber membrane type artificial lung comprising: a blood introduction port which is formed at an end of the inner cylinder and through which blood flows on the outside of the hollow fiber membrane; a hollow portion formed in the hollow fiber membrane into which oxygen is introduced so that a blood outside flowing method is employed; and a predetermined gap formed between the inner cylinder and the hollow fiber bundle. Furthermore, there is provided a method of arranging fiber for a hollow fiber membrane type artificial lung which has an inner cylinder, an outer cylinder, a hollow fiber bundle formed by collecting porous hollow fiber membrane and a supporting member for fluid-hermetically supporting the outer surface of the inner cylinder, the inner surface of the outer cylinder and the outer surface of the hollow fiber membrane at the two ends of the inner cylinder, the outer cylinder and the hollow fiber bundle in such a manner that the hollow fiber membrane is opened, the method of arranging fiber for a hollow fiber membrane type artificial lung comprising steps of: a step in which the hollow fiber bundle is collected and supplied to a cylindrical body having a diameter which is larger than that of the inner cylinder; and a step in which a predetermined gap is formed between the inner cylinder and the hollow fiber bundle by inserting the hollow fiber bundle into a space between the outer cylinder and the inner cylinder.

According to another aspect of the present invention, there is provided a membrane type artificial lung having a hollow fiber bundle formed by packing a gas permeable hollow fiber into a space formed by an inner cylinder thereof and an outer cylinder thereof, wherein a gas containing oxygen is allowed to flow in a hollow portion in the gas permeable hollow fiber and blood is allowed to flow on the outside of the gas permeable hollow fiber the membrane type artificial lung comprising: a bundle which is a component of the hollow fiber bundle and which is formed by twilling the gas permeable hollow fiber, a bundle which is a component of the hollow fiber bundle and which is formed by arranging the gas permeable hollow fiber in substantially the same direction as the lengthwise direction of each of the inner cylinder and the outer cylinder.

According to another aspect of the present invention, there is provided a hollow fiber membrane type artificial lung comprising: a cylindrical and annular hollow fiber bundle formed by, in a twilled manner, collecting and arranging a single or a plurality of gas permeable hollow fibers each of which has a space at the central portion thereof; an outer cylinder for accomodating the cylindrical and annular hollow fiber bundle; an inner cylinder which is inserted into a cylindrical space existing on inside of the annular hollow fiber bundle and which has a diameter which is smaller than the diameter of the cylindrical space; insulating walls for closing the two ends of the outer cylinder and an end of the inner cylinder in such a manner that the two ends of the hollow fiber membrane of the annular hollow fiber bundle are open, the insulating walls being composed of a first insulating wall which closes the ends of the outer cylinder and the inner cylinder and on which a first cap is capped which has an inlet or an outlet for gas containing oxygen which communicates with the internal space of the hollow fiber membrane and a second insulating wall which closes the ends of the outer cylinder but does not close the end of the inner cylinder and on which a second cap is capped which has an inlet or an outlet for gas containing oxygen which communicates with the internal space of the hollow fiber membrane; an annular blood-introduction passage which communicates with an internal space of the outer cylinder and fluid-hermetically independently formed from the second cap; and an annular blood-passage which is formed in the periphery of a portion near the top end of the outer cylinder and which communicates with a blood outlet.

According to another aspect of the present invention, there is provided a hollow fiber membrane type artificial lung accommodating a hollow fiber membrane serving as a gas exchanging membrane, the hollow fiber membrane type artificial lung comprising: a hollow fiber bundle formed by arranging a plurality of the hollow fibers to form elongated shapes and by winding the elongated hollow fibers while intersecting them at predetermined angles.

Other and further objects, features and advantages of the invention will be appear more fully from the following description.

PREFERRED EMBODIMENTS OF THE INVENTION

Preferred embodiments of the present invention will now be described with reference to the drawings.

Figure 1:
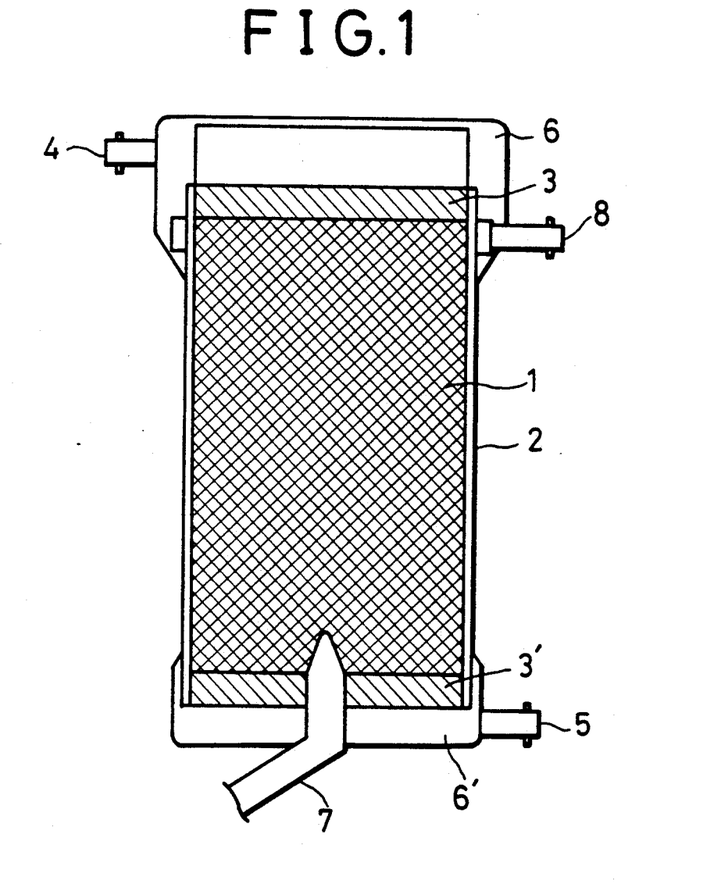
FIG. 1 is a cross sectional view which illustrates and embodiment of a hollow fiber membrane type artificial lung according to the present invention.

FIG. 1 illustrates an embodiment of a membrane type artificial lung. A hollow fiber bundle 1 formed by collectively twilling a single or a plurality of hollow fibers is accommodated in a casing 2. The hollow fiber bundle 1 is fastened to the two side portions of the casing 2 by insulating walls 3 and 3' made of potting material, while opening the two ends of the hollow fiber bundle. Head caps 6 and 6' are respectively provided for the insulating walls 3 and 3', the head caps 6 and 6' respectively having an inlet 4 and an outlet 5 through which a gas containing oxygen passes. The casing 2 has a blood inlet 7 at the central portion of at an end thereof, while the same has a blood outlet 8 in the vicinity of the insulating wall at another end thereof.

Referring to FIG. 1, blood passes through a blood port before it is introduced through the blood inlet 7. Subsequently, blood thus introduced passes through a space defined by the outer wall of the hollow fiber membrane and the inner wall of the casing 2 before it is discharged through the blood outlet 8. Since a space in which no hollow fiber membrane exists is formed in the vicinity of the blood inlet 7, significant effects of preventing a pressure loss and a drift can be obtained. That is, since the blood flow is not rapidly bent or narrowed in the blood inlet 7, the undesirable pressure loss can be prevented satisfactory. Furthermore, the channeling can be prevented.

The hollow fibers may be collected substantially in parallel to the casing or collected in a twilled manner. However, it is preferable that the hollow fibers be collected in the twilled manner for the purpose of preventing the drift (channeling).

The membrane type artificial lung according to this embodiment and shown in FIG. 1 is provided with the space in which no hollow fiber membrane exists in the vicinity of its blood inlet 7. The structure may be arranged in such a manner that the packing ratio of the hollow fiber membrane is increased from the central portion of the hollow fiber bundle to the inner wall of the casing. Another structure may be employed in which the packing ratio of the hollow fiber membrane is raised from the blood inlet portion toward the other side, that is, it is raised in the lengthwise direction of the fiber. All of the above-described structures are capable of realizing the above-described effect of preventing the pressure loss and the channeling.

The average packing ratio of the overall body of the hollow fiber bundle will be considered. Although the pressure loss can be prevented at a low packing ratio even if the blood flow is large (3 to 5 l/minute), the area of the blood passage is enlarged. In consequence, blood cannot completely reach the overall area of the hollow fiber bundle, and the channeling can easily be taken place. As a result, a satisfactory gas exchanging capability becomes deteriorated. If the packing ratio is raised (for example, 0.55 to 0.6), the gas exchanging capability can be improved. However, the blood passage area is reduced, causing the pressure loss to be enlarged. The artificial lung according to the present invention is able to overcome the above-described problems by employing the above-described structure. According to the present invention, there is provided an artificial lung arranged to have a large packing ratio but capable of preventing the pressure loss and channeling and revealing an excellent gas exchanging capability.

Then, a method of collecting and arranging the hollow fibers will be described.

The hollow fibers are supplied to the surface of a collecting rod or a collecting pipe while making a certain angle from the above-described surface so that the hollow fiber bundle is formed in the twilled manner on the collecting rod or pipe. The above-described term "twilled manner" means an arrangement of the hollow fibers while making a certain angle from the lengthwise direction of the inner or the outer pipe. Although a single hollow fiber membrane can be supplied, it is preferable that a plurality of elongated hollow fibers be supplied as shown in FIG. 2(b). In this case, since kinds of the hollow fibers can be prevented, the undesirable reduction of the effective membrane area can be prevented and the gas exchanging capability can be improved. In a case where a plurality of hollow fiber are supplied, 2 to 20 hollow fibers, preferably 4 to 6 hollow fibers are supplied while maintaining the elongated shape. If the number of the hollow fibers exceeds 10, a desired elongated shape cannot be realized. The angle of the twilling is arranged to be 100° to 170°, preferably 120° to 150°. Usually, a tension of 10 to 200 g, preferably 50 to 150 g, is applied to the hollow fiber at the time of collecting and arranging it. If the applied tension is too large, the hollow fiber bundle cannot move on the collecting rod without being damaged. The tension to be applied to the hollow fiber membrane can be adjusted so that the packing ratio at a specific portion of the hollow fiber bundle can be adjusted as desired. The packing ratio can be changed partially by changing the angle at which the hollow fibers is supplied to the surface of the collecting rod. That is, when the above-described angle is reduced, the packing ratio at that portion can be raised. When the angle is enlarged, the packing ratio can be reduced. Thus, by properly combining the tension, the angle and the shape of the collecting rod, the packing ratio of the hollow fiber bundle can be controlled. In consequence, a hollow fiber bundle of the most suitable structure can be obtained. After the hollow fibers have been collected and arranged, the collecting rod is removed from the hollow fiber rod. Although a cylindrical space is formed at the central portion of the hollow fiber bundle, it can easily be filled with the hollow fibers by external small force if the diameter of the collecting rod is arranged to be considerably small with respect to the diameter of the hollow fiber bundle.

The diameter of the collecting rod is not limited if it has the strength to perform the collecting operation. A tapered collecting rod or a collecting rod the diameter of which is not equal may be employed so that the packing ratio can be changed in desired portions of the hollow fiber bundle. Furthermore, the hollow fiber bundle must be shifted from the surface of the collecting rod into the housing after the hollow fiber bundle has been collected and arranged. Therefore, it is preferable that the surface of the collecting rod be coated with fluororesin in order to enable the hollow fiber bundle to be shifted smoothly without being damaged.

It is preferable that the hollow fiber membrane for use in the artificial lung according to the present invention is made of polypropylene. Furthermore, the following synthetic resin may be employed: polyethylene, polytetrafluoroethylene, polysulfon, polyacrylonitrile, polyurethane and silicon.

The hollow fiber membrane bundle may be made of a porous material or a non-porous material. In the case where the hollow fiber membrane is made of the porous material, it is preferable that the small apertures formed on the wall surface have an average diameter of 0.01 to 1 $\mu$m. Furthermore, the percentage of voids must be 20 to 80%. In addition, the overall area of the hollow fiber membrane to be enclosed in the housing must be about 3 $m^2$ or less.

Figure 2:
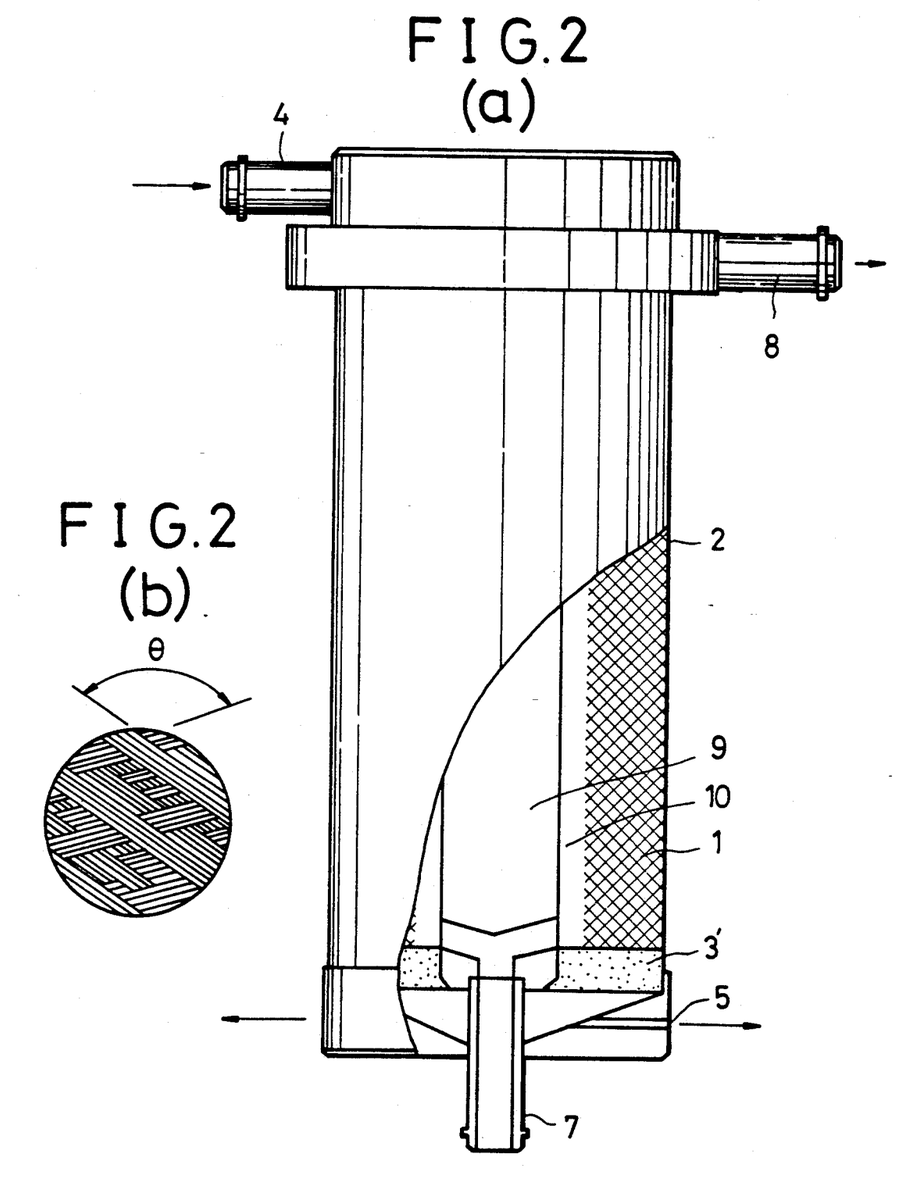
FIG. 2(a) is a cross sectional view which illustrates another embodiment of the artificial lung according to the present invention.
FIG. 2(b) is a partially enlarged view which illustrates a state of a collection of hollow fiber in a hollow fiber bundle.

FIG. 2 is a cross sectional view which illustrates another embodiment of the present invention.

Referring to FIG. 2, blood is introduced into the blood inlet 7 through the blood port. Blood, which has passed through the blood inlet 7 is subsequently and partially introduced into the hollow fiber bundle 1 before it is introduced into a gap portion 10 formed between an inner cylinder 9 and the hollow fiber bundle 1. Then, blood gradually flows into the overall body of the hollow fiber bundle 1. In consequence, the blood passage is not rapidly narrowed at the blood inlet 7, causing the pressure loss to be prevented.

Referring to FIG. 2, reference numeral 8 represents the blood outlet, 4 represents the gas (oxygen) inlet and 5 represents a gas outlet.

It is preferable that the gap formed between the inner cylinder and the hollow fiber bundle is 1 mm to 10 mm on one side of a portion from the outer surface of the inner cylinder to the inner surface of the hollow fiber bundle, further preferably 2 mm to 5 mm. Furthermore, although it is preferable that the gap has a uniformly formed between the inner cylinder and the hollow fiber bundle, the present invention is not limited to this.

Then, a method of collecting and arranging the hollow fibers for use in the artificial lung shown in FIG. 2 will be described below:

First, the hollow fiber bundle composed of the hollow fibers is temporarily collected and arranged at the surface of a cylindrical body (collecting cylinder) having a diameter larger than that of the inner cylinder. The collected and arranged hollow fiber bundle is inserted into a space formed between the outer cylinder and the inner cylinder so that the predetermined gap is formed between the inner cylinder and the hollow fiber bundle. Thus, the hollow fiber membrane bundle of the artificial lung according to this embodiment can be collected and arranged.

The diameter of the collecting cylinder must be larger than that of the inner cylinder. It is preferable that the difference between the diameter of the collecting cylinder and that of the inner cylinder be 2 mm or more, preferably, 4 to 10 mm.

Another embodiment of the artificial lung according to the present invention will be described below with reference to FIG. 6.

Figure 6:
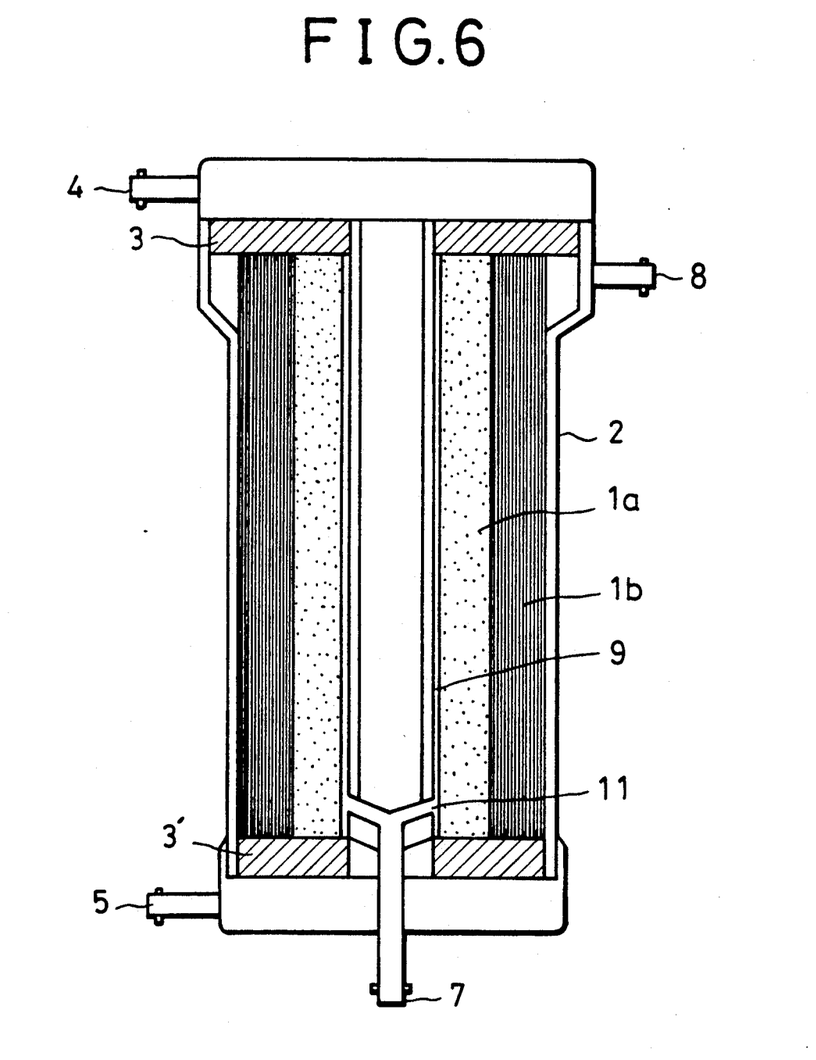
FIG. 6 is cross sectional view which illustrates another embodiment of the hollow fiber membrane artificial lung according to the present invention.

The artificial lung shown in FIG. 6 is made of at least two layers arranged in such a manner that a portion in the vicinity of the portion to which blood flows is formed by a twilled or woven hollow fiber bundle so that the drifting flow is prevented. Furthermore, its periphery portion is made of a hollow fiber bundle in which the hollow fibers are linearly arranged so that the pressure loss is prevented.

In the membrane type artificial lung according to this embodiment, blood which has been equally introduced from the blood inlet portion into the flow passage distributed between hollow fiber pieces flows into the twilled portion, blood subsequently equally flowing there while preventing the generation of a drift.

Blood distributed equally in the twilled portion is subsequently and directly introduced into the portion in which the fiber is linearly arranged to flow into an outlet portion of the artificial lung, where the "portion in which the fiber is linearly arranged" includes the structure in which the fiber is distributed in parallel to the lengthwise direction of the inner cylinder or the outer cylinder and as well as includes the structure in which the fiber is wound while making an acute angle from that direction. The present invention is not limited to the ratio of the thickness of the hollow fiber bundle in the twilled portion and that in the portion in which the fiber is arranged linearly. However, it is preferable that the thickness of the hollow fiber bundle in the portion in which the fiber is arranged to be relatively larger than the other portion.

The membrane artificial lung according to this embodiment may be arranged in such a manner that the hollow fiber membrane may directly be wound around the surface of the inner cylinder. As an alternative to this, another structure may be employed in which it is wound to the surface of a cylinder having a diameter larger than the outer diameter of the inner cylinder and that hollow fiber bundle is removed from the cylinder before the obtained hollow fiber bundle is disposed between the inner cylinder and the outer cylinder. In the above-described case in which the hollow fiber bundle is directly wound to the surface of the inner cylinder, the winding density must be restricted so as to prevent the pressure loss which can be enlarged due to a reduction in the cross sectional area of the blood passage, the reduction being caused if the winding density is too high. If a gap is formed between the surface of the inner cylinder and the inner surface of the hollow fiber bundle, the above-described problem can be overcome.

Then, the membrane artificial lung according to this embodiment will specifically be described below.

The artificial lung according to this embodiment comprises the outer cylinder (casing) 2, the inner cylinder 9 the lower end of which is closed, a hollow fiber bundle 1a of the twilled portion disposed in a gap between the two cylinders 2 and 9, a hollow fiber bundle 1b in which the hollow fiber membrane is linearly arranged and a potting (insulating wall) portions 3 and 3' secured in such a manner that its two ends are secured while opening the hollow fibers.

Blood is introduced through the blood inlet 7 before it successively passes through a blood introducing portion 11, the hollow fiber bundle 1a of the twilled portion and the hollow fiber bundle 1b in which hollow fiber membrane is linearly arranged. Subsequently, blood is discharged from the blood outlet 8 formed at an end portion opposing the portion into which blood in the outer cylinder 2 is introduced.

A gas is introduced through the gas inlet 4 before it passes through the inner portion of the hollow fiber. The gas is subsequently discharged through the gas outlet 5.

It is preferable that the gas permeable hollow fiber membrane is first wound around the cylinder having a diameter which is larger than the inner diameter of the inner cylinder by several millimeters. The gas permeable hollow fiber membrane is wound at a twilling angle (an angle made from the axial direction of the cylinder) of, for example, 125° until the thickness of the wound layer becomes the half of the total thickness of the same to be wound. Subsequently, the gas permeable hollow fiber membrane is wound in the same direction as the axial direction of the cylinder. Then, the thus collected hollow fiber bundle is disposed in a gap formed between the inner cylinder and the outer cylinder before its two ends are secured by the potting material. The undesirable channeling can be prevented thanks to the existence of the twilled portion near the inner cylinder. The packing ratio (the ratio of the area in which the hollow fiber exists and the overall cross sectional area) of the hollow fiber in the twilled portion is arranged to be 0.4 to 0.7, preferably 0.55 to 0.6. The packing ratio in the portion in which the hollow fiber membrane is linearly arranged is not limited.

Then, another embodiment of the artificial lung according to the present invention will be described with reference to FIG. 7.

Figure 7:
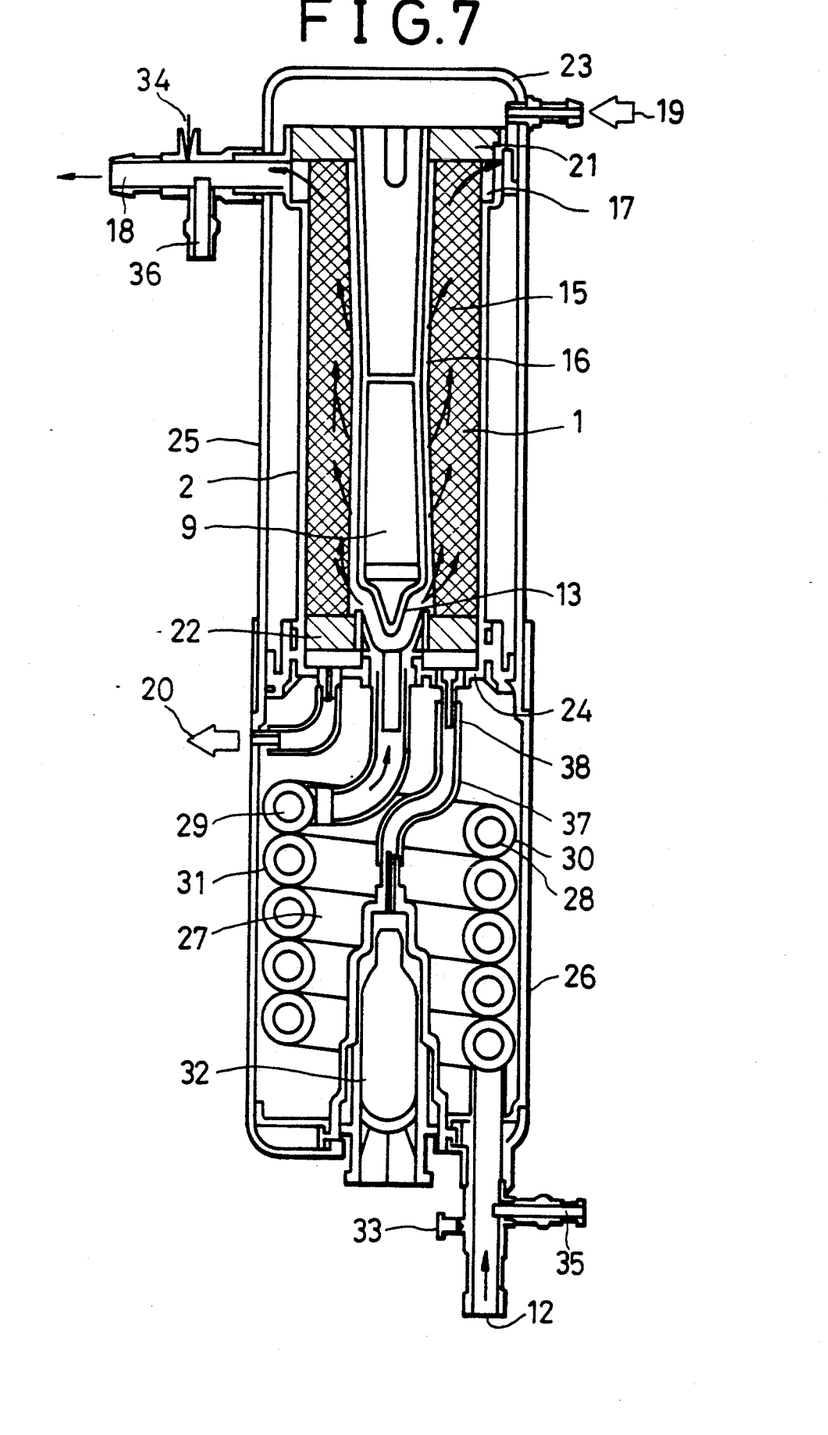
FIG. 7 is a cross sectional structural view which illustrates another embodiment of the present invention.

Referring to FIG. 7, blood passes through a blood inlet 12 before it is introduced into an annular chamber 15 formed between the outer cylinder 2 and the inner cylinder 9 through an annular blood-introduction passage 13 formed in the lower portion of the inner cylinder 9 having a diameter which is smaller than a cylindrical space formed inside the annular hollow fiber bundle 1. A portion of blood is introduced into the annular hollow fiber bundle 1, while the other portion of blood is introduced into a gap 16 formed between the inner cylinder 9 and the annular hollow fiber bundle 1. Subsequently, blood gradually spreads into the overall body of the annular hollow fiber bundle 1 so as to flow outside the hollow fiber membrane in the annular hollow fiber bundle 1 until it reaches an annular blood-passage 17 formed in the periphery of a portion near the top end of the outer cylinder 1. Subsequently, blood is discharged through a blood outlet 18.

During blood flow, as described, in the overall body of the annular hollow fiber bundle 1, blood is subjected to a gas exchange with a gas containing oxygen which has been introduced through a gas inlet 19 and which is flowing in the hollow fiber membrane. In consequence, oxygen is given to blood, while carbon dioxide is removed so as to be discharged through a gas outlet.

In the artificial lung shown in FIG. 7, blood is smoothly introduced into the annular chamber 15 formed between the outer cylinder 2 and the inner cylinder 9. Subsequently, a portion of blood is introduced into the annular hollow fiber bundle 1, while the outer portion of the same is introduced into the gap 16 formed by the inner cylinder 9 and the annular hollow fiber bundle 1. As a result, the blood flow is not rapidly warped or the same is not rapidly narrowed. Therefore, the pressure loss can be prevented.

Subsequently, blood radially flows in the annular hollow fiber bundle 1 in which it is subjected to the gas exchange. Then, blood is introduced into an annular blood-passage 17 formed in the periphery near the top end of the outer cylinder 2 disposed at a position opposing the end of the annular blood-introduction passage 13. As a result of the thus arranged structure, blood is able to uniformly and equally flow. As a result, the drift of blood can be prevented.

The artificial lung shown in FIG. 7 comprises a gas exchanging portion I and a heat exchanging portion II which is integrally formed with the gas exchanging portion I below the gas exchanging portion I. The heat exchanging portion II includes a carbon dioxide cartridge 32.

In the gas exchanging portion I, the annular chamber 15 formed between the outer cylinder 2 and the inner cylinder 9 accommodates the annular hollow fiber bundle 1 arranged to be in the form of the cylindrical shape and formed by collecting a single or a plurality of gas permeable hollow fibers in a twilled manner.

In order to make the two ends of the hollow fiber membrane which forms the annular hollow fiber bundle 1 to be opened at the two ends of each of the outer cylinder 2 and the inner cylinder 9, the two ends of the outer cylinder 12 and an end of the inner cylinder 9 are supported by the insulating walls in such a manner that they are closed. A first insulating wall 21 of the two insulating walls closes both the end of the outer cylinder 2 and that of the inner cylinder 9, while a second insulating wall 22 closes the end of the outer cylinder 2 but it does not close the end of the inner cylinder 9.

A first cap 23 having the gas inlet 19 which communicates with the internal space in the hollow fiber membrane and through which the gas containing oxygen is introduced is capped on the first insulating wall 21. On the other hand, a second cap 22 having the gas outlet 20 which comminicates with the internal space in the hollow fiber membrane and through which the gas containing oxygen is discharged is capped on the second insulating wall 22. The second insulating wall 22 has the annular blood-introduction passage 13 which communicates with the annular chamber 15 of the outer cylinder 2 and hermetically independent from the second cap 24.

It is preferable to form the blood inlet 12 or outlet 18 which communicates with the annular chamber 15 formed in the central portion of the second insulating wall 22 and between the outer cylinder 2 and the inner cylinder 9 and which is liquid hermetically independent from the first cap 23.

It is also preferable to make the end portion of the annular hollow fiber bundle 2 which is supported by the first insulating wall 21 to be positioned on the same surface as the outer surface of the first insulating wall 21 or a position inner than that (that is, to be shortened). In addition, it is preferable to make the end portion of the inner cylinder 9 (inner core) adjacent to the second insulating wall 22 to be in the form a projection. In consequence, blood can smoothly be introduced into the annular chamber 15.

Furthermore, it is preferable to make the diameter of the annular blood-introduction passage 13 to be made smaller than the outer diameter of the inner cylinder 9 by about 5 mm and simultaneously smaller than the inner diameter of the annular hollow fiber bundle 1.

The annular blood-passage 17 which communicates with the blood outlet 18 is formed in the periphery near the top end of the outer cylinder 2.

In addition, the outer surface of the outer cylinder 2 is covered by a decorative cylinder 25 via a space.

The heat exchanging portion II is integrally formed with the gas exchanging portion I in the lower portion of the gas exchanging portion I. The outer housing 26 of the heat exchanging portion II has a heat exchanger 27 including a heat exchanging tube for maintaining the temperature of blood at a predetermined level. The heat exchanger 27 is constituted by spirally winding the heat exchanging tube in the form of a duplex tube. According to this embodiment, the inner space of the inner tube 28 is arranged to be a water passage 29 through which water passes, while a space between the inner tube 28 and the outer tube 30 is arranged to be a blood passage 31 through which blood passes. A carbon dioxide cartridge 32 is loaded into the inner space of the heat exchanger 27 of the heat exchanging portion II so that carbon dioxide is introduced from the carbon dioxide gas cartridge 32 into a carbon dioxide gas inlet 38 formed in the second cap 24 via a tube 37, the carbon dioxide gas being used at the time of priming.

Blood collecting ports 33 and 34 and temperature measuring ports 35 and 36 are respectively formed in the vicinity of the blood inlet 12 and the blood outlet 18.

In the thus constituted structure, blood passes through the blood inlet 12 so as to be introduced into the blood passage 31 formed in the heat exchanger 27. In consequence, blood is subjected to the heat exchange with water which is passing through the water passage 29 so that a desired temperature is realized. Subsequently, blood is introduced from the annular blood-introduction passage 13 into the annular chamber 15, causing a portion of the same to be introduced into the annular hollow fiber bundle 1. On the other hand, the other portion of blood is introduced into the gap 16 formed between the inner cylinder 9 and the annular hollow fiber bundle 1. Then, blood gradually spreads into the overall body of the annular hollow fiber bundle 1, and it flows outside the hollow fiber membrane in the annular hollow fiber bundle 1 until it reaches the annular blood passage 17 formed in the periphery neat the top end of the outer cylinder 2. Then, blood is discharged through the blood outlet 18.

As described above, blood is subjected to the gas exchange during it flows through the overall body of the annular hollow fiber bundle 1 so that oxygen is given to blood from the gas containing oxygen and flowing in the hollow fiber membrane after it has been introduced through the gas inlet 19. Furthermore, the carbon dioxide is removed.

Figure 11A:
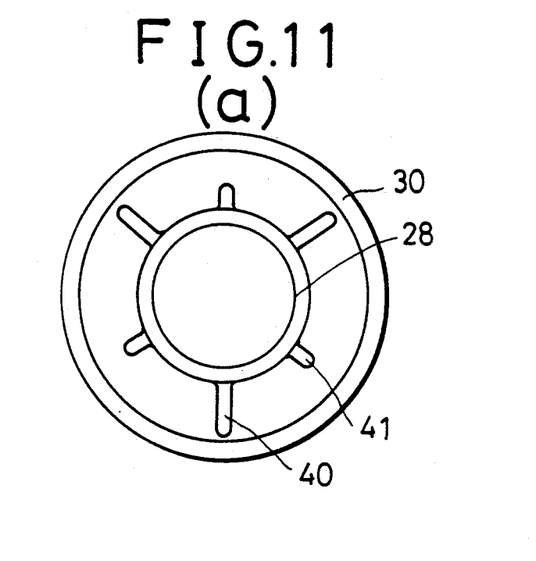
FIG. 11(a) is a cross sectional view which illustrates a tube of a heat exchanger in a direction perpendicular to the lengthwise direction of the same.
Figure 11B:
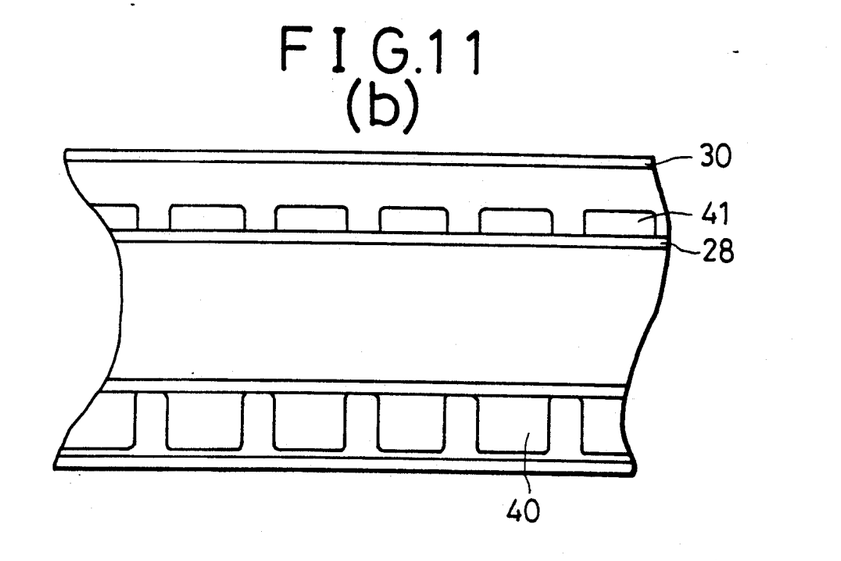
FIG. 11(b) is a cross sectional view which illustrates a portion of the tube of the heat exchange in a lengthwise direction.

It is preferable for the heat exchanger 27 to comprise a duplex tube type heat exchanger composed of the inner tube 28 and the outer tube 30 and arranged in such a manner that ribs 40 and 41 having lengths to approach the inner wall of the outer tube 30 are formed on the outer surface of the inner tube 28 in the lengthwise direction of the inner tube 28, as shown in FIG. 11(a) and 11(b).

The structure must be arranged in such a manner that at least two ribs 40 and 41 are formed on the outer wall of the inner tube 28 in the circumferential direction of the inner tube 28. Although it is not necessary for the thus formed ribs to be disposed at the same interval, they are usually formed at an interval of an angular degree of 180°. The ribs can be provided for three places at angular intervals of 120°, four places at angular intervals of 90° or more places if necessary to correspond to the diameter, the thickness of the wall or the curvature of the spiral of each of the inner wall 28 and the outer tube 30 of the duplex tube. However, it is preferable to provide the ribs for three or four places in consideration of the flow and the pressure loss. Furthermore, although the ribs 40 and 41 may be continuously formed in the lengthwise direction, cutouts can be formed in optional portions in the lengthwise direction in order to satisfactorily reduce the pressure loss if the deformation taken place due to forming the spiral structure can be prevented. In addition, the both the ribs 40 and 41 must not have the length to the position adjacent to the inner wall of the outer tube 30. Rib such as the rib 41 serving as a sub-rib having a shorter length may be employed together with the main rib 40 having the length substantially reaching the inner wall of the outer tube 30 in order to improve the heat exchanging efficiency.

EXAMPLE 1

The surface of the collecting rod having an outer diameter of 4 mm was coated with fluororesin, and the hollow fibers were collected on the fluororesin layer. After the hollow fibers had been collected into a bundle, the hollow fiber bundle was moved on the collecting rod so that it is removed. Simultaneously, the hollow fiber bundle was placed in the housing so that the artificial lung the dimensions of which were as follows and constituted as shown in FIG. 1 was manufactured. The tension applied to the collected hollow fibers was 100 g in the former process, while it was 150 g in the process.

| | | |
|---|---|---|
| Collecting Rod: | Length | 350 mm |
| | Outer diameter | 4 mm |
| | Surface | Fluororesin coating |
| Housing 2: | Outer diameter | 64 mm |
| | Length | 200 mm |
| Pourous Hollow Fiber film | Inner diameter | about 300 μm |
| | Outer diameter | about 400 μm |
| | Average diameter of small apertures | 0.22 mm |
| | Void ratio | 65 to 70% |
| | Material | polypropylene 4 |
| Hollow Fiber Bundle 2: | Length | 280 mm |
| | Twilling angle | 130° |
| | Packing ratio | 0.594 |
| | Quantity of Charged Blood | 170 cc |
| | Potting Material | polyurethane |

The above-described artificial lung was subjected to a performance test by using the fresh blood of cattle which was Standard Venous Blood regulated by AAMI (Association for Advance of Medical Instrumentation). Blood of cattle was introduced into the above-described artificial lung.

The gas exchanging performance was evaluated at blood flows of 1 l/minute, 3 l/minute and 5 l/minute. Also the pressure loss preventing performance was evaluated at the same blood flows of 1 l/minute, 3 l/minute and 5 l/minute. The blood collection and the measurement of the pressure were performed at positions near the blood inlet and the blood outlet formed in the artificial lung. A gas analyzer was used to measure the oxygen pressure, the saturation ratio, the carbon dioxide pressure, the quantity of the carbon dioxide and pH-value of the collected blood. Subsequently, a quantity of the gas transfer and that of the carbon dioxide transfer were calculated. The oxygen gas was supplied to the artificial lung so as to cause the ratio of the blood flow and the oxygen gas flow to be 1:1.

The pressure loss, the quantity of the oxygen transfer and that of the carbon dioxide transfer were respectively 30, 40, 140 mmHg, 60, 190, 310 ml/minute, 60, 150 and 200 ml/minute at the blood flows of 1 l/minute, 3 l/minute and 5 l/minute.

As can be understood from the above described data, the artificial lung according to this example reveals an excellent gas exchanging performance while satisfactorily preventing the pressure loss.

EXAMPLE 2

A collecting pipe the outer diameter of which was 30 mm and the surface of which was coated with fluororesin was manufactured, and the hollow fiber was collected. After the hollow fiber had been collected into a bundle, the hollow fiber bundle was moved on the collecting pipe so that it was removed. Simultaneously, the hollow fiber bundle was introduced into the space between the inner cylinder and the outer cylinder so that the artificial lung having the following dimensions and constituted as shown in FIG. 2 was manufactured, where the tension to be applied to the hollow fiber at the time of collecting the same was arranged to be 100 g in the former stage and 150 g in the latter stage.

| Collecting Pipe: | |
| --- | --- |
| Length | 350 mm |
| Outer diameter | 30 mm |
| Surface | Fluororesin coating |
| Diameter of the outer cylinder 2 | 64 mm |
| Diameter of the inner cylinder 9 | 25 mm |
| Inner diameter of the porous hollow fiber membrane | about 300 μm |
| Outer diameter of the porous hollow fiber membrane | about 400 μm |
| Average diameter of the small apertures | 0.22 mm |
| Void ratio | 65 to 70% |
| Material | polypropylene |
| Hollow fiber bundle 1 | twilling angle θ = 130° (see FIG. 2B) |
| Length of the hollow fiber bundle 1 | 280 mm |
| Potting material | polyurethane |
| Interval between the outer surface of the inner cylinder 9 and the inner surface of the hollow fiber bundle 1 | 2.5 mm for one side (5 mm in all) |

Table 1 shows the specifications of each of the artificial lungs.

TABLE 1

|  | A | B | C | D | E |
| --- | --- | --- | --- | --- | --- |
| Length of module | 180 | 200 | 180 | 180 | 180 |
| Void Ratio | 0.6 | 0.6 | 0.47 | 0.5 | 0.63 |
| Remarks | gap exists | gap exists | gap exists | gap exists | gap exists |

The artificial lungs thus constituted and having the specifications above were subjected to performance test by using fresh blood of cattle which was Standard Venous Blood regulated by AAMI (Association for Advance of Medical Instrumentation). Blood of cattle was introduced into the above-described artificial lungs.

The gas exchanging performance was evaluated at blood flows of 1 l/minute and 3 l/minute. The pressure loss preventing performance was evaluated at the blood flows of 1 l/minute, 3 l/minute and 5 l/minute. The blood collection and the measurement of the pressure were performed at positions near the blood inlet and the blood outlet formed in each of the artificial lungs. A gas analyzer was used to measure the oxygen pressure, the saturation ratio, the carbon dioxide pressure, the quantity of the carbon dioxide and pH-value of the collected blood. Subsequently, a quantity of the gas transfer and that of the carbon dioxide transfer were calculated. The oxygen gas was supplied to each of the artificial lungs so as to cause the ratio of the blood flow and the oxygen gas flow to be 1:1.

Figure 3:
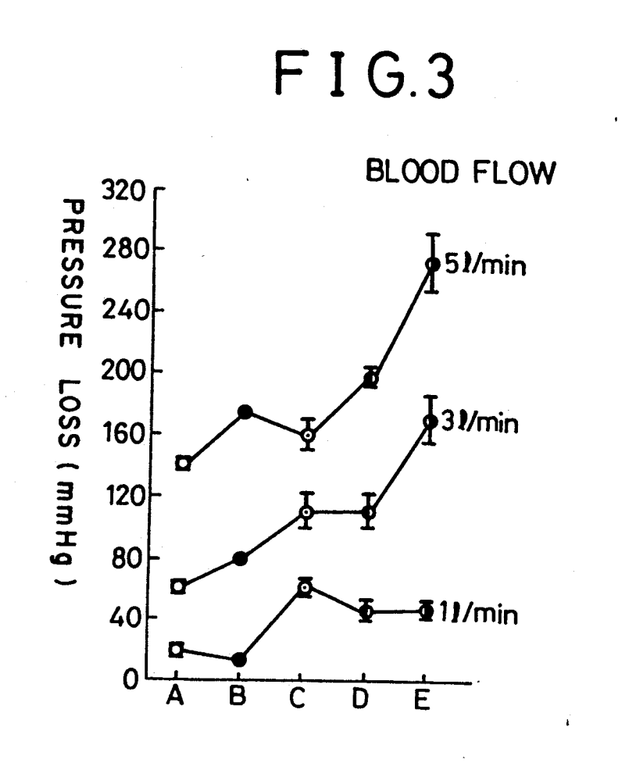
FIGS. 3 to 5 are graphs which respectively show a pressure loss, a quantity of oxygen transfer and a quantity of carbon dioxide transfer with respect to specifications of the artificial lungs according to the embodiments.
Figure 4:
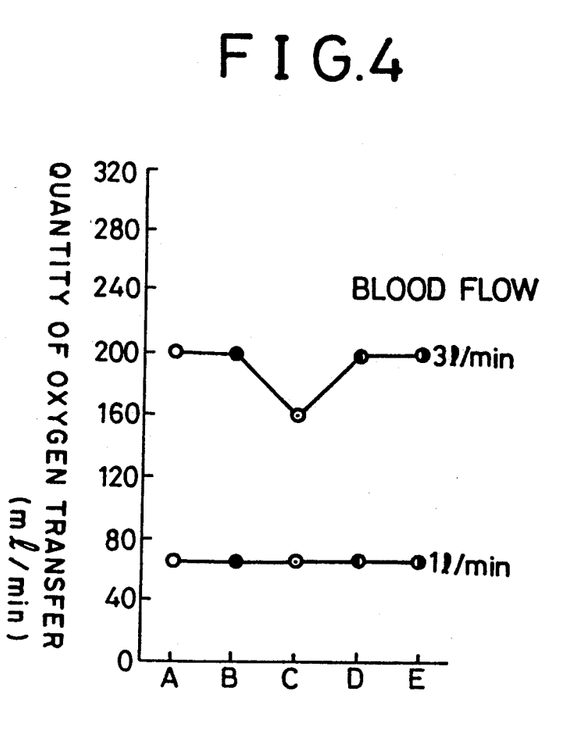
Figure 5:
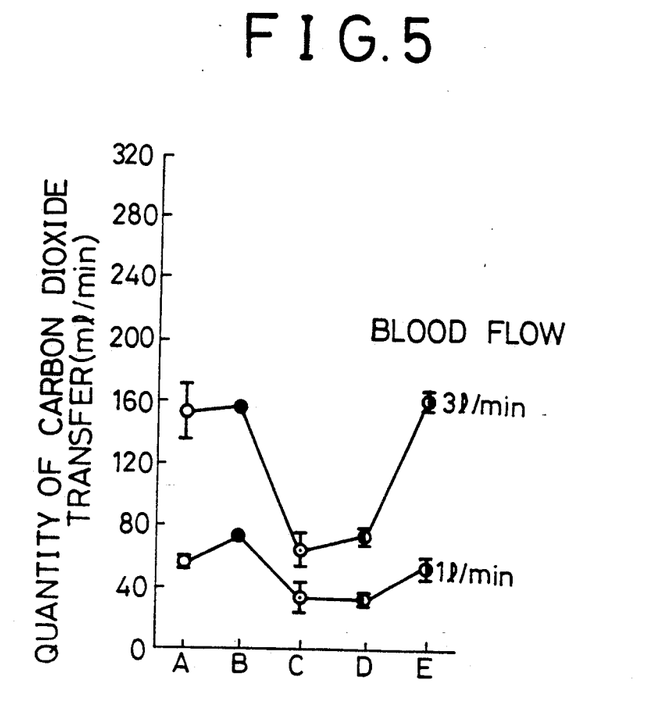

The results of the measurements of the pressure loss, the quantity of the oxygen transfer and that of the carbon dioxide transfer are shown in FIGS. 3, 4 and 5.

As can be seen from FIG. 3, a satisfactory pressure loss preventing performance was obtained from the artificial lung having a gap between the inner cylinder and the hollow fiber bundle thereof in comparison to the artificial lung having no gap. A satisfactory result which was equivalent or more satisfactory value was obtained although having a void ratio of 0.6 in comparison to the artificial lung the void ratio of which was arranged to be 0.47 and which has not gap.

As can be clearly seen from FIGS. 4 and 5, unsatisfactory gas exchanging performance was displayed in the artificial lungs each of which had no gap and the packing ratio of which were 0.47 and 0.5. A satisfactory gas exchanging performance was obtained from the artificial lung the packing ratio of which was 0.63. The artificial lung the packing ratio of which was 0.6, which is, by 0.03, lower than that of the artificial lung the packing ratio of which was 0.63 displayed a satisfactory gas exchanging performance equivalent to that obtainable from the artificial lung the packing ratio of which was 0.63.

EXAMPLE 3

The specifications of the artificial lung constituted as shown in FIG. 6 and according to Example 3 were as follows:

Inner diameter of the hollow fiber: 300 μm
Outer diameter of the hollow fiber: 400 μm
Outer diameter of the twilled portion: 42 mm
Outer diameter of the linearly arranged portion: 58 mm
Ratio of packing the hollow fiber: 0.6
Twilling angle: 125°
Gap between the inner surface of the hollow fiber bundle and the outer surface of the inner cylinder: about 2 mm
Effective length: 180 mm
Effective membrane area: 1.7 m².

The procedure of testing the gas exchanging performance of the thus constituted membrane type artificial lung according to Example 3 and results of evaluations were as follows:

Blood of cattle was used in the tests. Standard Venous Blood having the following properties was prepared by an adjusting artificial lung. The Standard Venous Blood was subsequently introduced into each of the artificial lung to be tested. Then, blood was collected at the blood inlet and outlet of each of the artificial lungs so as to measure the pH-value, the oxygen gas pressure and the carbon dioxide gas pressure and the like by using the blood gas analyzer so that the quantity of the oxygen gas transfer and that of the carbon dioxide gas transfer were calculated.

Properties of the Standard Venous Blood

Saturation ratio of oxygen: 65±5%
Quantity of hemoglobin: 12±1 g/dl
Carbon dioxide pressure: 45±5 mmHg
Temperature of blood: 37°±2° C.
BE (Base Excess): 0±5 meq/l.

The oxygen gas was supplied to each of the artificial lungs so as to cause the ratio of the blood flow and the oxygen gas flow to be 1:1.

Then, the results of the experiments will be described.

The quantity of oxygen transfer and that of carbon dioxide gas transfer in the artificial lungs according to the present invention and calculated from the results of the blood gas analysis respective were 65 ml/minute and 50 ml/minute at a blood flow of 1 l/minute, 195 ml/minute and 140 ml/minute at a blood flow of 3 l/minute and 320 ml/minute and 240 ml/minute at a blood flow of 5 l/minute. The pressure loss was 20, 70, 130 mmHg at the blood flow of 1, 3 and 5 l/minute.

EXAMPLE 4

A collecting pipe the outer diameter of which was 30 mm and the surface of which was coated with fluororesin was manufactured, and the hollow fibers were collected. After the hollow fibers had been collected into a bundle, the annular hollow fiber bundle was moved on the collecting pipe so that it was removed. Simultaneously, the hollow fiber bundle was introduced into the space between the inner cylinder and the outer cylinder so that the artificial lung having the following dimensions and constituted as shown in FIG. 7 was manufactured, where the tension to be applied to the hollow fiber membrane at the time of collecting the same was arranged to be 100 g in the former stage and 150 g in the latter stage.

| Collecting Pipe: | |
| --- | --- |
| Length | 350 mm |
| Outer diameter | 30 mm |
| Surface | Fruororesin coating |
| Diameter of the outer cylinder (outer casting) | 58 mm |
| Diameter of the inner cylinder (inner core) | 25 mm |
| Inner diameter of the porous hollow fiber membrane | about 300 μm |
| Outer diameter of the porous hollow fiber membrane | about 400 μm |
| Average diameter of the small apertures | 0.22 mm |
| Void ratio | 65 to 70% |
| Material | polypropylene |
| Hollow fiber bundle | twilling angle θ = 130° |
| Effective length of the annular hollow fiber bundle | 180 mm |
| Supporting member | polyurethane resin |
| Interval between the outer surface of the inner cylinder and the inner surface of the hollow fiber bundle | 2.5 mm for one size (5 mm in all) |
| Inner diameter of the annular blood-introduction passage | 21 mm |
| Width of slit formed in the annular blood-introduction passage | 8 mm |
| Annular blood-passage | an annular passage the cross sectional area of which was 4 × 10 mm and the inner diameter of which was 58 mm |

The artificial lungs thus constituted and having the specifications above were subjected to a performance test by using fresh blood of cattle which was Standard Venous Blood regulated by AAMI (Association for Advance of Medical Instrumentation). Blood of cattle was introduced into the above-described artificial lungs.

The gas exchanging performance was evaluated at blood flows of 1 l/minute, 3 l/minute and 5 l/minute. Also the pressure loss preventing performance was evaluated at the same blood flows of 1 l/minute, 3 l/minute and 5 l/minute. The blood collection and the measurement of the pressure were performed at positions near the blood inlet and the blood outlet formed in the artificial lung. A gas analyzer was used to measure the oxygen pressure, the saturation ratio, the carbon dioxide pressure, the quantity of the carbon dioxide and pH-value of the collected blood. Subsequently, a quantity of the gas transfer and that of the carbon dioxide transfer were calculated. The oxygen gas was supplied to the artificial lung so as to cause the ratio of the blood flow and the oxygen gas flow to be 1:1.

Figure 8:
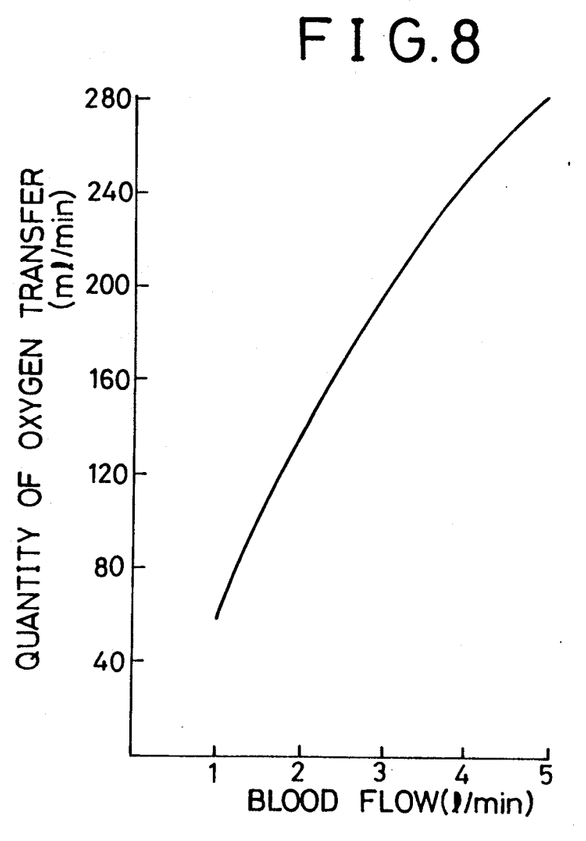
FIG. 8 is a graph which illustrates the quantity of oxygen transfer.
Figure 9:
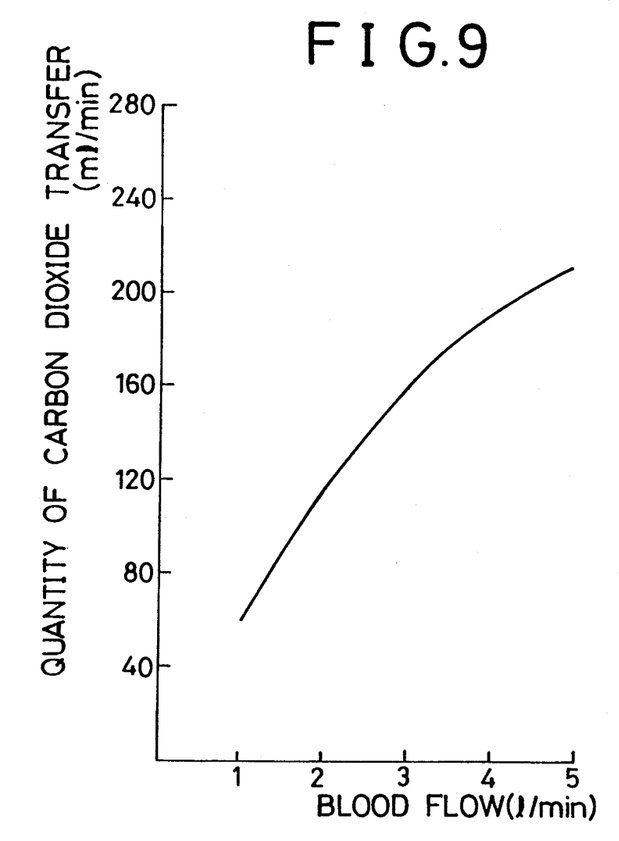
FIG. 9 is a graph which illustrates the quantity of carbon dioxide gas transfer.
Figure 10:
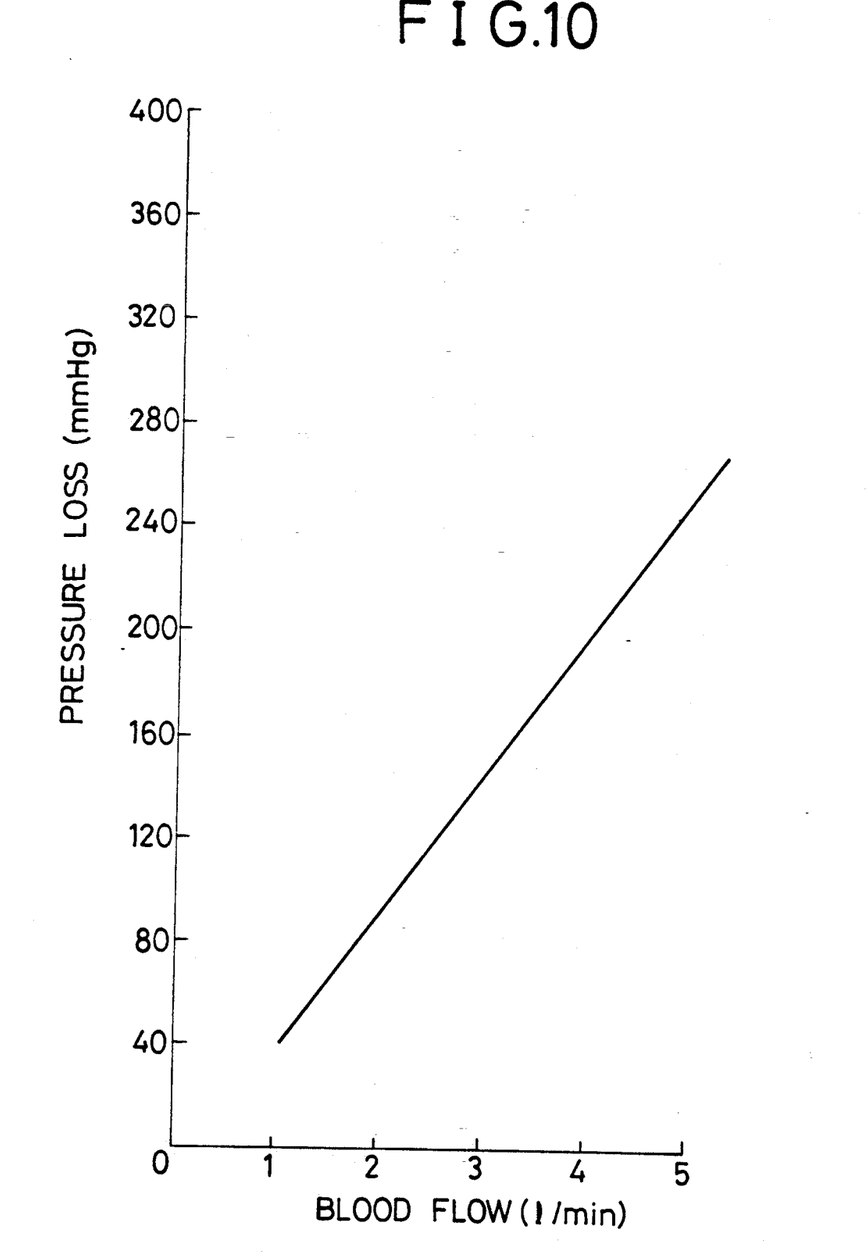
FIG. 10 is a graph which illustrates the pressure loss of the artificial lung.

The results were as shown in FIGS. 8, 9 and 10.

As can be clearly seen from the above-described results, a satisfactorily large quantity of gas transfer and carbon dioxide transfer were obtained while considerably preventing the pressure loss. Therefore, it can be understood that a satisfactory gas exchanging performance can be realized.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

What is claimed is:

1. A hollow fiber membrane type artificial lung comprising:

a casing having two ends and an inner wall and which accommodates a hollow fiber bundle having two ends and comprising a hollow fiber membrane having two ends and an outer wall, and a potting material for supporting and securing said hollow fiber bundle at positions near the two ends of said casing in such a manner that the two ends of the hollow fiber membrane are opened, said hollow fiber bundle being packed in an internal space of said casing wherein a packing ratio of said hollow fiber membrane is arranged in such a manner that it is changed from sparse in a central portion of said hollow fiber bundle to dense toward said inner wall of said casing;

oxygen supply means for supplying a gas containing oxygen to said casing so that the gas containing oxygen flows in a space in said hollow fiber membrane; and blood supply means for supplying blood to said casing at a center location of a bottom end of said two ends of said casing so that blood flows in a space defined by the outer wall of said hollow fiber membrane and the inner wall of said casing.

2. A hollow fiber membrane type artificial lung comprising an inner cylinder having two ends, an outer cylinder having two ends, a hollow fiber bundle having two ends and formed by collecting a porous hollow fiber membrane, a supporting member for supporting an outer surface of said inner cylinder, an inner surface of said outer cylinder and an outer surface of said hollow fiber bundle at the two ends of each of said inner cylinder, said outer cylinder and said hollow fiber bundle in such a manner that said hollow fiber membrane is opened, a gap being formed between the outer surface of said inner cylinder and an inner surface of said hollow fiber bundle;

blood supply means comprising a blood introduction port for supplying blood to said artificial lung via said blood introduction port so that blood flows outside of said hollow fiber membrane; and oxygen supply means for supplying a gas containing oxygen to said artificial lung so that the oxygen is introduced into a hollow portion formed in said hollow fiber membrane.

3. A hollow fiber membrane type artificial lung according to claim 1 or 2, further comprising a heat exchanger composed of an inner tube and an outer tube, the heat exchanger being arranged in such a manner that ribs having lengths to approach an inner wall of the outer tube are formed on the outer surface of an inner tube in the lengthwise direction of the inner tube.

* * * * *